US009579045B2

United States Patent
Galjan et al.

(10) Patent No.: US 9,579,045 B2
(45) Date of Patent: Feb. 28, 2017

(54) LENGTH MEASURING DEVICE

(71) Applicant: Seca AG, Reinbach (CH)

(72) Inventors: Wjatscheslaw Galjan, Nützen (DE); Jan Schmidt, Bargteheide (DE); Andreas Nessler, Hamburg (DE); Bernd Krause, Stelle (DE)

(73) Assignee: seca ag (CH)

( * ) Notice: Subject to any disclaimer, the term of this patent is extended or adjusted under 35 U.S.C. 154(b) by 118 days.

(21) Appl. No.: 14/648,093

(22) PCT Filed: Aug. 16, 2013

(86) PCT No.: PCT/EP2013/067144
§ 371 (c)(1),
(2) Date: May 28, 2015

(87) PCT Pub. No.: WO2014/082763
PCT Pub. Date: Jun. 5, 2014

(65) Prior Publication Data
US 2016/0213283 A1 Jul. 28, 2016

(30) Foreign Application Priority Data
Nov. 28, 2012 (DE) .......................... 10 2012 220 412

(51) Int. Cl.
*A61B 5/107* (2006.01)
*G01B 17/00* (2006.01)
*G01B 17/02* (2006.01)

(52) U.S. Cl.
CPC ............ *A61B 5/1072* (2013.01); *G01B 17/02* (2013.01); *A61B 2560/0223* (2013.01); *A61B 2562/0204* (2013.01)

(58) Field of Classification Search
CPC .............................. A61B 5/1072; G01B 17/00
(Continued)

(56) References Cited

U.S. PATENT DOCUMENTS

| 6,982,929 B2 * | 1/2006 | Moss ................... A61B 5/1072 181/124 |
| 7,006,405 B1 * | 2/2006 | Huang ..................... G01S 7/521 367/107 |

(Continued)

FOREIGN PATENT DOCUMENTS

| CH | DE 102014016468 A1 * | 6/2016 | ........... A61B 5/1072 |
| DE | 3428132 A1 | 6/1985 | |

(Continued)

OTHER PUBLICATIONS

S.S. Huang et al., A High Accuracy Ultrasonic Distance Measurement System Using Binary Frequency Shift-Keyed Signal and Phase Detection, Review of Scientific Instruments, vol. 73, No. 10, pp. 3671-3677 (Oct. 2002).

(Continued)

*Primary Examiner* — Christopher Fulton
(74) *Attorney, Agent, or Firm* — Hovey Williams LLP

(57) ABSTRACT

The invention relates to a length measuring device having a measuring slide, a linear guide in the form of a hollow profile, on which the measuring slide is mounted so it is externally displaceable, an inner slide, which is mounted so it is displaceable in the interior of the hollow profile, a magnet assembly, which magnetically couples measuring slide and inner slide, so that the inner slide follows every movement of the measuring slide along the hollow profile, a measuring unit for measuring the position of the inner slide, and a display, which is visible in the exterior of the hollow profile, of the length ascertained by the measuring unit in accordance with the measured position of the inner slide. The measuring unit has a sound source, a sound receiver, and a control and analysis unit connected thereto.

17 Claims, 9 Drawing Sheets

Figure 4:
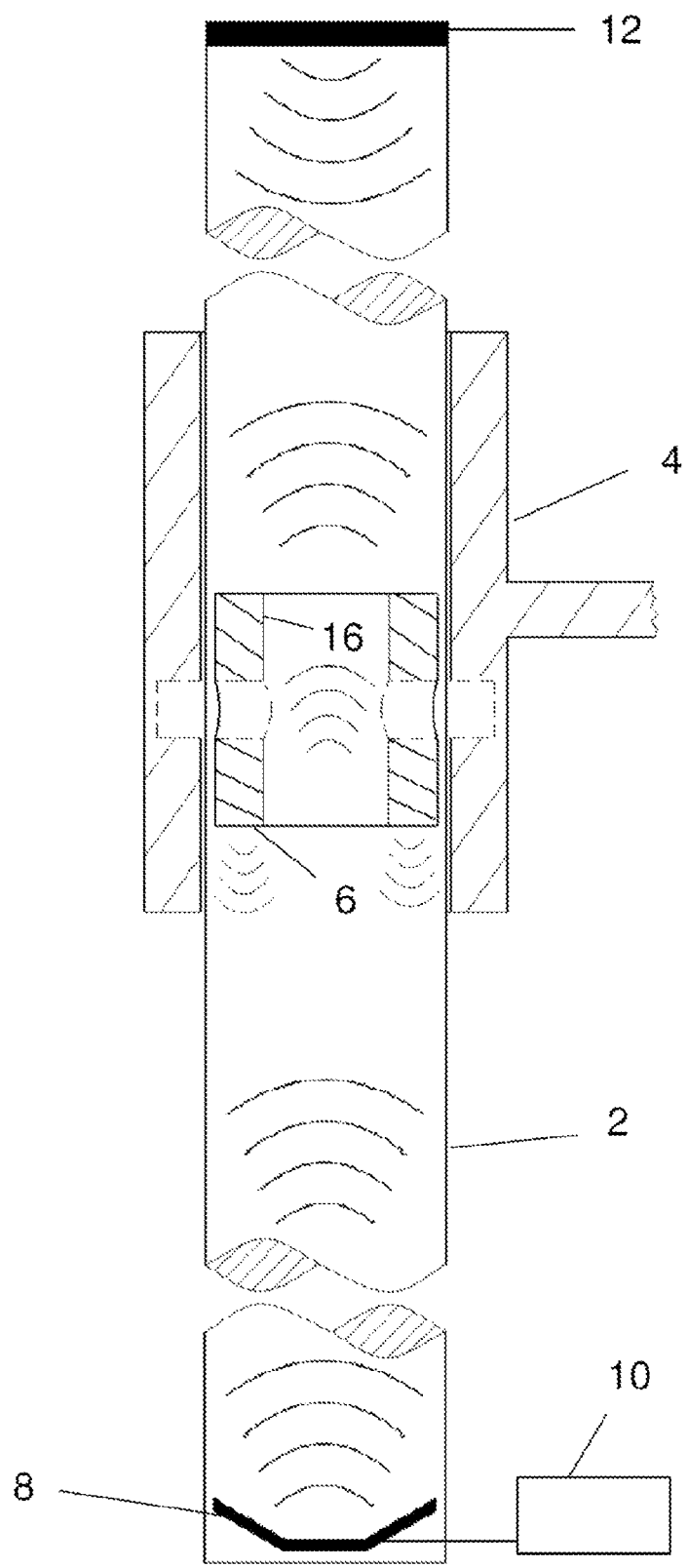

(58) Field of Classification Search
USPC .............................. 33/512; 367/108, 107, 99
See application file for complete search history.

(56) References Cited

U.S. PATENT DOCUMENTS

| | | | | |
|---|---|---|---|---|
| 7,200,952 | B2* | 4/2007 | Montagnino | A61B 5/0537 33/512 |
| 8,845,332 | B1* | 9/2014 | Reid | A61B 5/1072 33/512 |
| 2005/0059902 | A1* | 3/2005 | Itagaki | A61B 5/0537 600/547 |
| 2008/0196505 | A1* | 8/2008 | Weichao | G01B 17/00 73/597 |
| 2014/0071270 | A1* | 3/2014 | Vogel | A61B 5/1072 348/135 |
| 2014/0318256 | A1* | 10/2014 | Perisse | G01P 13/00 73/627 |
| 2015/0085613 | A1* | 3/2015 | Petersen | F15B 15/2884 367/99 |
| 2015/0168247 | A1* | 6/2015 | Gundersen | G01S 13/08 342/118 |
| 2016/0242676 | A1* | 8/2016 | Grossmann | A61B 5/1072 |

FOREIGN PATENT DOCUMENTS

| | | |
|---|---|---|
| DE | 19700966 C1 | 4/1998 |
| DE | 102007037980 A1 | 8/2008 |
| DE | 102012220412 B3 | 3/2014 |
| JP | 5882110 | 5/1983 |
| JP | 02239843 | 9/1990 |
| WO | 8501800 A1 | 4/1985 |
| WO | 9817974 A1 | 4/1998 |
| WO | 0037886 A1 | 6/2000 |

OTHER PUBLICATIONS

R. Queiros et al., A New Method for High Resolution Ultrasonic Ranging in Air, XVIII Imeko World Congress, Metrology for a Sustainable Development, Rio de Janeiro, Brazil (Sep. 17, 2006).

M.M. Saad et al., Robust High-Accuracy Ultrasonic Range Measurement System, IEEE Transactions on Instrumentation and Measurement, vol. 60, No. 10, pp. 3334-3341 (Oct. 2011).

Translation of Written Opinion from PCT Application No. PCT/EP2013/067144 entitled Length Measuring Device (Dated Apr. 11, 2013).

* cited by examiner

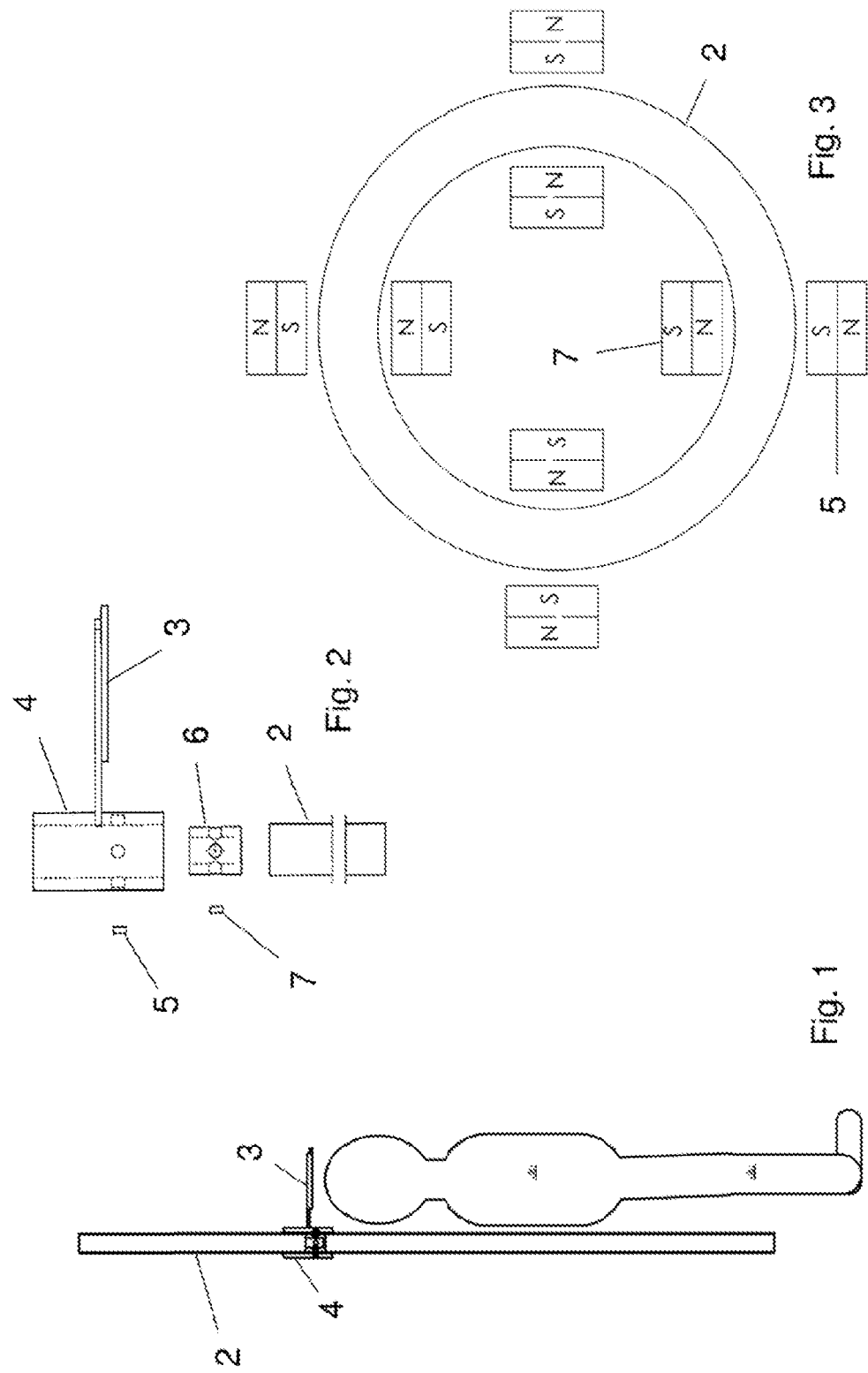

LENGTH MEASURING DEVICE

CROSS-REFERENCE TO RELATED APPLICATIONS

This is a National Phase Application pursuant to 37 C.F.R. §371 of International Application No. PCT/EP2013/067144, filed Aug. 16, 2013, claiming priority from German Application No. DE 10 2012 220 412.1, filed Nov. 28, 2012, the entire disclosures of which are hereby incorporated by reference herein.

BACKGROUND OF THE INVENTION

1. Field of the Invention

The present invention relates to a length measuring device having a measuring slide, a linear guide in the form of a hollow profile, on which the measuring slide is mounted so it is externally displaceable, to be able to bring it into contact with an object to be measured with respect to its length, an inner slide, which is mounted so it is displaceable in the interior of the hollow profile, a magnet assembly, which magnetically couples the measuring slide and the inner slide so that the inner slide follows every movement of the measuring slide along the hollow profile, a measuring unit for measuring the position of the inner slide along the hollow profile, and a display, which is visible in the exterior of the hollow profile, of the length ascertained by the measuring unit in accordance with the measured position of the inner slide.

2. Discussion of the Prior Art

The invention is directed in particular to length measuring devices for measuring the physical height of persons. Such length measuring devices are also referred to as stadiometers. A typical such length measuring device has a measuring rod, which is implemented as a vertical linear guide for a measuring slide (head slide). The measuring rod is aligned vertically and is installed on a wall or fastened on a platform. To measure the physical height, the person steps in front of the measuring rod, after which the head slide is pushed down on the measuring rod until it comes into contact on the head of the person to be measured. A measuring scale having scale graduation lines is provided on the measuring rod. A read unit is in turn provided in the measuring slide, which registers the scale graduation lines during the displacement of the measuring slide on the measuring rod and therefore detects the incremental change of the position of the measuring slide. The absolute height of a scale graduation line can also be coded in the scale graduation lines, so that the height of the head slide can be determined using the read unit, which is then displayed on a display on the measuring slide.

Another type of a length measuring device for the physical height has an angled part, which is held by a person carrying out the measurement of the physical length. A leg of the angled part is held in contact on the head of the person to be measured. A second leg protrudes perpendicularly from this leg in contact on the head, wherein the angled part is held so that the second leg extends directed vertically towards the floor. A distance measuring unit having an ultrasonic transducer is provided in the second leg, which, from the runtime of an emitted ultrasound signal, which is reflected on the floor and returns to the ultrasonic transducer, determines the height of the first leg located in contact on the head of the person to be measured above the floor and therefore the physical height and displays it. A disadvantage of this type of length measuring device is that measurement inaccuracies can occur because the person carrying out the measurement does not hold the angled part exactly aligned so that the second leg is oriented precisely vertically on the floor. Furthermore, it is disadvantageous that changing environmental conditions (for example, dust or other contaminants in the air) or objects lying on the floor could corrupt the measurement.

A further type of a length measuring device has a platform, onto which the person to be measured steps, and a horizontal support fixedly suspended vertically above the person to be measured. A distance measuring unit based on ultrasound wave runtime is attached to the support, which is directed towards the head of the person to be measured, who is standing on the platform. The person to be measured wears a cap to ensure a well-defined reflection of the ultrasound waves from the upper side of the head. The physical length of the person to be measured may be derived from the distance of the upper side of the head of the person to the distance measuring unit, which is permanently installed horizontally above the person to be measured, from the difference of the suspension height of the distance measuring unit and the measured distance to the upper side of the head. This length measuring device is also susceptible to error, since the measurement can be corrupted by changing environmental conditions and interfering influences in the open measuring section between the ultrasonic transducer and the upper side of the head of the person to be measured.

A length measuring device is disclosed by WO 98/17974 A1. This length measuring device is not implemented as a length measuring device for persons. Rather, the position of a measuring slide is to be tracked. The length measuring device has a linear guide in the form of a hollow housing, on which the measuring slide is mounted so it is externally displaceable. In the interior of the housing, an inner slide is mounted so it is displaceable therein. A magnet assembly couples the measuring slide and the inner slide magnetically, so that the inner slide follows every movement of the measuring slide along the guide. The inner slide is in slip contact with a linear potentiometer to provide a voltage signal, which is proportional to a position of the inner slide. The position of the inner slide and therefore that of the measuring slide coupled thereto along the linear guide is derived from the potentiometer signal. Certain interfering factors such as smoke or dust, which do not penetrate into the interior of the housing, are reduced in their influence on the measurement precision by the measurement of the position of the inner slide in the interior of the housing. The potentiometer has slip contacts, which create abrasion and thus wear over time. To counteract this, high-quality materials must be used, which increases the production costs, of course. However, the wear can result in worsening of the measurement precision even under these conditions.

SUMMARY

It is the object of the present invention to implement a length measuring device so that it offers a high measurement precision independently of variable environmental conditions, in particular it offers the possibility of carrying out reference measurements for calibration of the length measurement.

A length measuring device comprising a measuring slide, a linear guide, an inner slide, a magnet assembly, a measuring unit, and a display is used to achieve this object. The linear guide comprises a hollow profile, on which the measuring slide is mounted so as to be externally displaceable, to be able to bring the measuring slide into contact with an object to be measured with respect to an object length. The inner slide is mounted so as to be displaceable in an interior of the hollow profile. The magnet assembly magnetically couples the measuring slide and inner slide, so that the inner slide follows every movement of the measuring slide along the hollow profile. The measuring unit is for measuring a position of the inner slide along the hollow profile. The display, which is visible in an exterior of the hollow profile, is of a measured object length ascertained by the measuring unit in accordance with the measured position of the inner slide. The measuring unit includes a sound source, a sound receiver, and a control and analysis unit connected to the sound source and the sound receiver. The control and analysis unit is configured to excite the sound source to emit a sound signal and to analyze representative output signals of the sound receiver, to determine a runtime of a first reflected sound signal reflected on the inner slide at a reflection location and to calculate the position of the inner slide along the hollow profile. The control and analysis unit is furthermore configured to capture a further reflected sound signal represented in the output signals of the sound receiver, wherein the further reflected signal has been reflected at a known point along the hollow profile or at a known distance from the reflection location of the first reflected sound signal, and to cause a runtime of the further reflected sound signal to be incorporated as a reference measurement in the calculation of the position of the inner slide. Advantageous embodiments of the invention, including details of construction, are discussed herein.

It is provided according to the invention that the measuring unit has a sound source and a sound receiver in the interior of the hollow profile and also a control and analysis unit connected thereto. The control and analysis unit is configured to excite the sound source to emit a sound signal and to analyze output signals of the sound receiver, to determine a runtime of the sound signal after being reflected on the inner slide and to calculate the position of the inner slide along the linear guide therefrom. The hollow profile and/or the inner slide are embodied so that a further reflection signal generated at another known point occurs. The control and analysis unit is furthermore configured to capture the further reflected signal and to have its runtime incorporated as a reference measurement in the calculation of the position of the inner slide.

In this manner, the position of the measuring slide can be obtained on the basis of the position of the inner measuring slide independently of changing atmospheric environmental conditions, such as dust in the air and the like, since the measurement in the interior of the hollow profile is substantially shielded in relation thereto. Furthermore, by way of the measurement of a further reflected signal, with known position of the reflection point of the further reflected signal or with known distance to the reflection location of the first signal reflected on the inner slide, a calibration of the calculation of the position of the inner slide can be carried out, so that variable environmental conditions such as the ambient temperature and ambient humidity can also be compensated for.

A reference measurement does not have to be carried out during each determination of the position of the inner slide, of course. It is sufficient if a reference measurement is repeated occasionally for renewed calibration.

In an advantageous embodiment, the sound source is arranged on one end of the hollow profile. Furthermore, the inner slide has a ring-shaped structure having a passage opening. In the case of such a structure, firstly a sound signal is reflected on the lower wall region of the ring-shaped slide. A further reflection point is represented by the upper edge of the passage opening, which faces away from the sound source, since sound waves are also reflected back to the sound receiver from this edge. With known axial length of the passage opening through the inner slide, an absolute calibration of the length calculation may thus be carried out from the difference of the runtime measurements of the two reflected signals. To amplify the formation of the further reflected signal on the upper edge of the passage opening of the inner slide, a protrusion, which protrudes into the opening of the passage opening, for example, can be provided on the upper edge, on which a part of an ultrasound signal passing the passage opening of the inner slide is reflected.

Since the distance of the further reflection location (in this case the axial length of the inner slide) is known, the control and analysis unit, after detection of the first reflected sound signal, can search in a specific time window for the further reflected sound signal, since the approximate interval between the two reflected signals is known (except for variations due to variable ambient temperature and ambient humidity).

In a further advantageous embodiment, the inner slide again has a ring-shaped structure having a passage opening. The control and analysis unit is adapted to detect a sound signal reflected on the inner slide and determine its runtime. In addition, the end of the hollow profile opposite the sound source is closed with a wall. The control and analysis unit is furthermore configured to detect a sound signal which has passed through the passage opening of the inner slide and has been reflected on the wall of the opposing end of the hollow profile and to derive a calibration for the calculation of the position of the inner slide from the runtime measurement from its runtime with known length of the hollow profile.

In a preferred embodiment, discontinuities (reflection points) can also be arranged on the inner wall of the hollow profile at predetermined positions, which generate reflected sound signals, which can be detected as further reflected sound signals, to thus determine further runtimes for known reflection points along the hollow profile.

In a preferred embodiment, the hollow profile of the length measuring device is completely closed, so that variable atmospheric environmental conditions have no influence on the measurement in the interior of the hollow profile, which is shielded in relation thereto.

The control and analysis unit is preferably configured to carry out the distance determination via a TOF method (time of flight). Such methods are known in the prior art, for which reference is made, for example, to the articles "A high accuracy ultrasonic distance measurement system using binary frequency shift-keyed signal and phase detection", by S. S. Huang et al., Review of Scientific Instruments, volume 73, issue 10, October 2002, pages 3671-3677, "A new method for high resolution ultrasonic ranging in air" by R. Queiros et al., XVIII Imeko World Congress, Metrology for a Sustainable Development, Sep. 17-22, 2006, Rio de Janeiro, Brazil, and "Robust High-Accuracy Ultrasonic Range Measurement System" by M. M. Saad et al., IEEE Transactions on Instrumentation and Measurement, volume 60, issue 10, October 2011, pages 3334-3341.

To carry out a TOF method, the control and analysis unit can also be configured to excite the sound source with a periodic excitation signal, to which a characteristic signal property such as a phase jump, an amplitude jump, or a frequency jump is superimposed, and to calculate the runtime by forming a correlation of the reflected signals recorded by the sound receiver with the excitation signal. In particular, a cross-correlation can be calculated between the mentioned signals and the runtime can be determined at the maximum of the cross-correlation.

In a preferred embodiment, the magnet assembly has at least one permanent magnet on the measuring slide and one permanent magnet on the inner slide, which are arranged so that opposite poles of the two permanent magnets are aligned in relation to one another facing toward one another. Preferably, four permanent magnets are arranged in relation to one another in each case on the inner slide and on the measuring slide so that in each case, one pair of a permanent magnet on the measuring slide and on the inner slide are aligned in relation to one another having opposite poles facing toward one another. Alternatively, the magnet assembly only has one permanent magnet on one of measuring slide and inner slide, wherein then the other component of measuring slide and inner slide contains ferromagnetic or paramagnetic material, so that measuring slide and inner slide are magnetically coupled.

The external dimensions of the inner slide are preferably adapted to the internal dimensions of the hollow profile so that the inner slide is seated without play, but so it can slide in the hollow profile. The internal dimensions of the measuring slide are accordingly adapted to the external dimensions of the hollow profile so that the measuring slide is mounted without play, but so it can slide externally on the hollow profile.

The internal diameter of the hollow profile is preferably selected and the sound source and the control and analysis unit are preferably configured so that the internal diameter of the hollow profile is less than half of the wavelength of the sound waves of the sound signal. It is therefore ensured that the sound propagates as a flat wave in the hollow profile. With shorter wavelengths, the sound could also propagate in other modes, i.e., it would be reflected on the walls and therefore cover a longer distance.

These modes effectively have a lower speed of sound and are overlaid on the signal of the flat wave slightly offset in time. The frequency should fundamentally be selected to be as high as possible, to obtain a high time resolution. The mentioned condition may be implemented well in particular in the case of the use of sound signals having acoustic sound wavelengths (acoustic sound signals refer here and hereafter to signals having sound wavelengths in the range audible by the human ear).

In a preferred embodiment, the sound source is an ultrasound source and the sound receiver is an ultrasound receiver. In particular in this case, the ultrasound source and the ultrasound receiver can be formed by a unified ultrasonic transducer in the form of a transceiver.

In an alternative embodiment, the sound source can have a loudspeaker for generating an acoustic sound signal and the sound receiver can have a microphone for recording acoustic sound signals.

BRIEF DESCRIPTION OF THE DRAWING FIGURES

Figure 5:
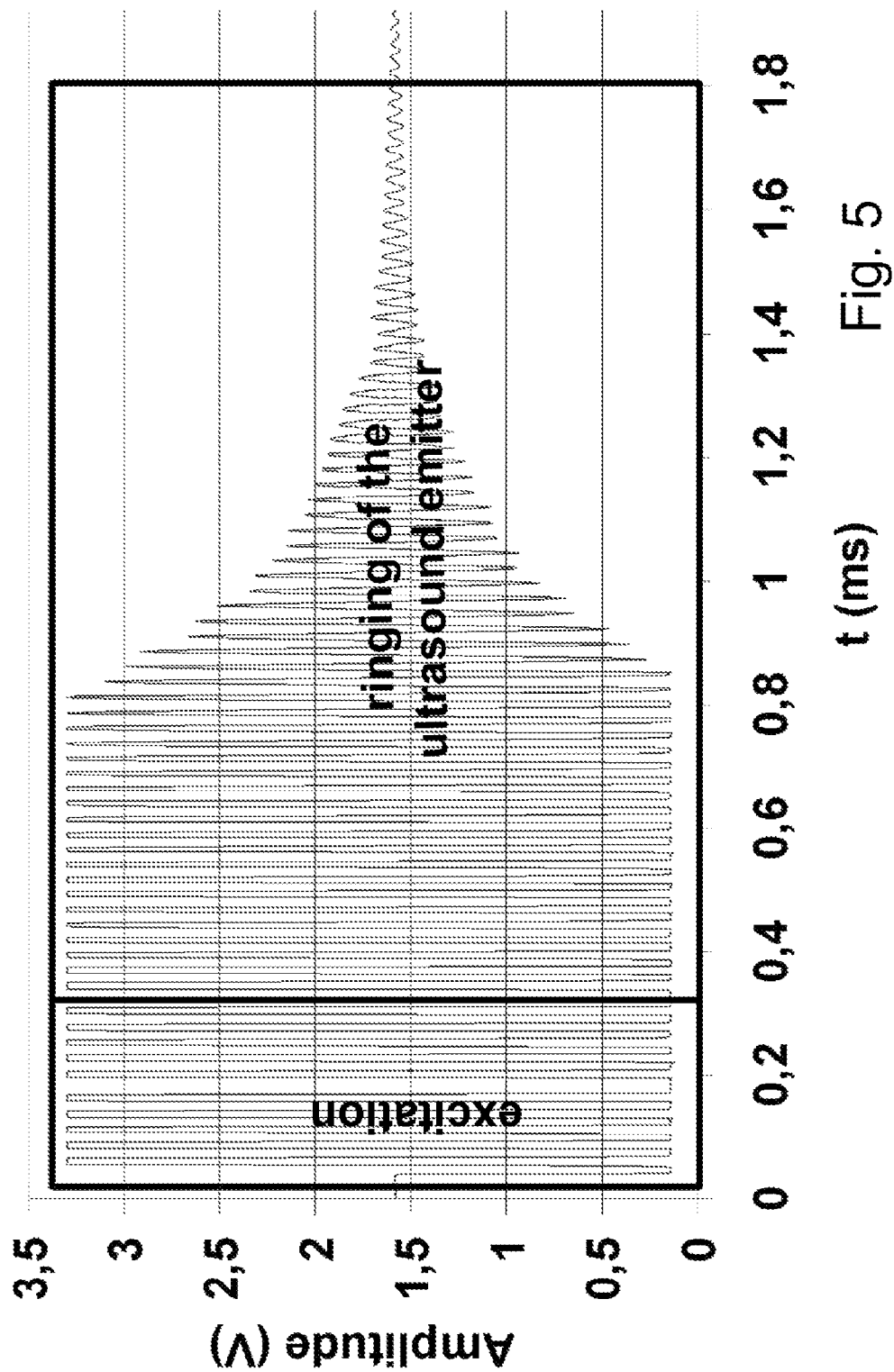
Figure 6:
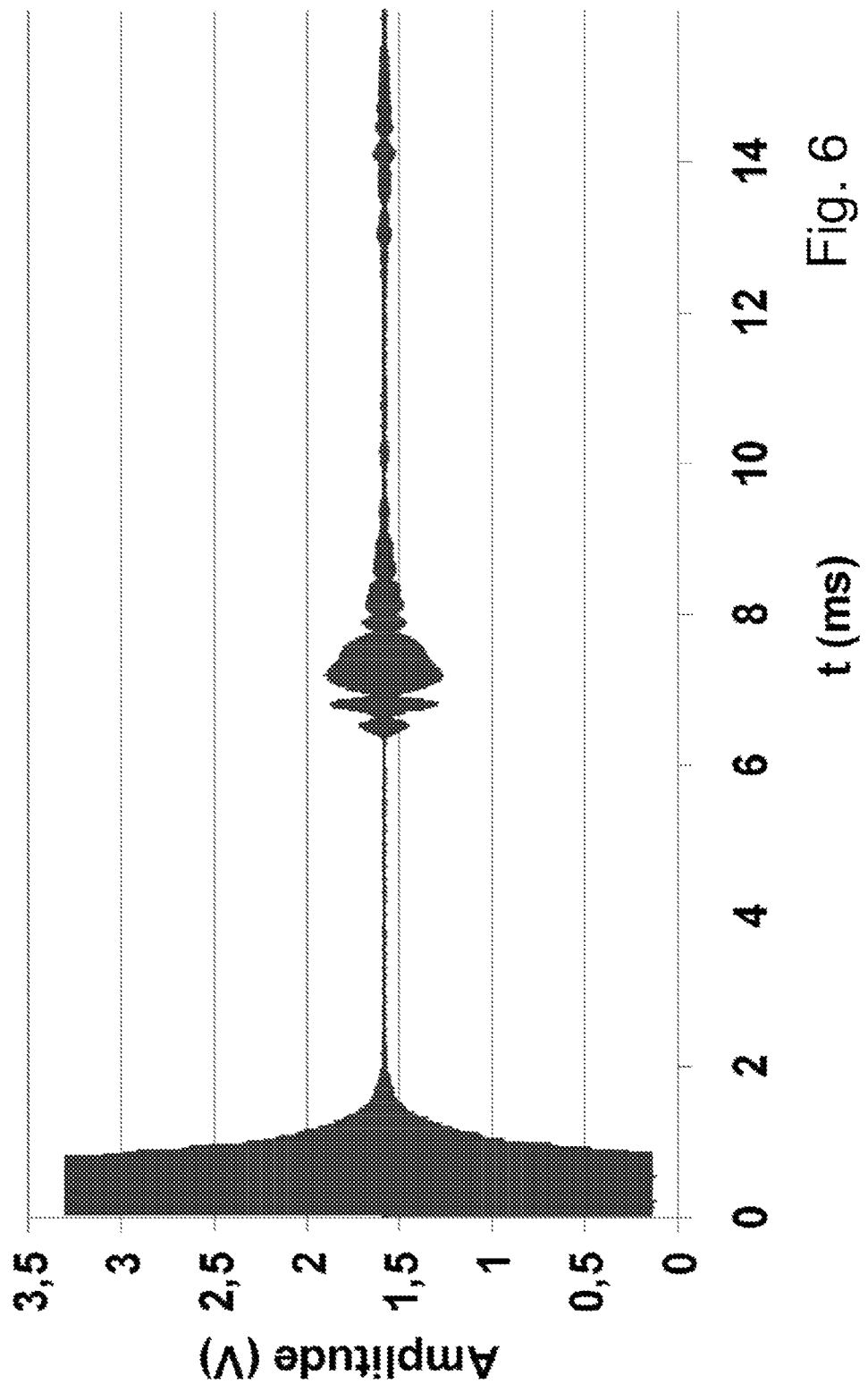
Figure 7:
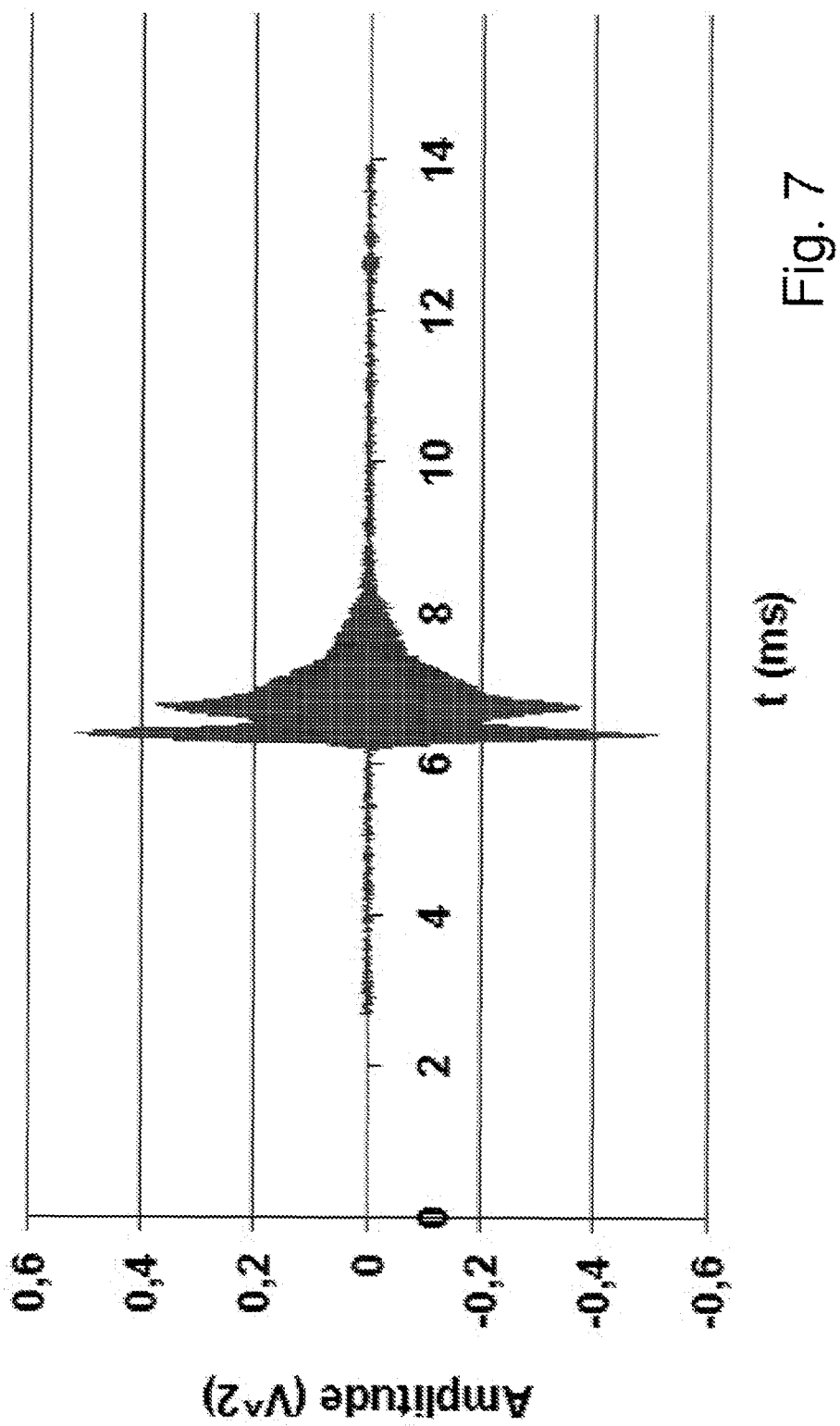
Figure 8:
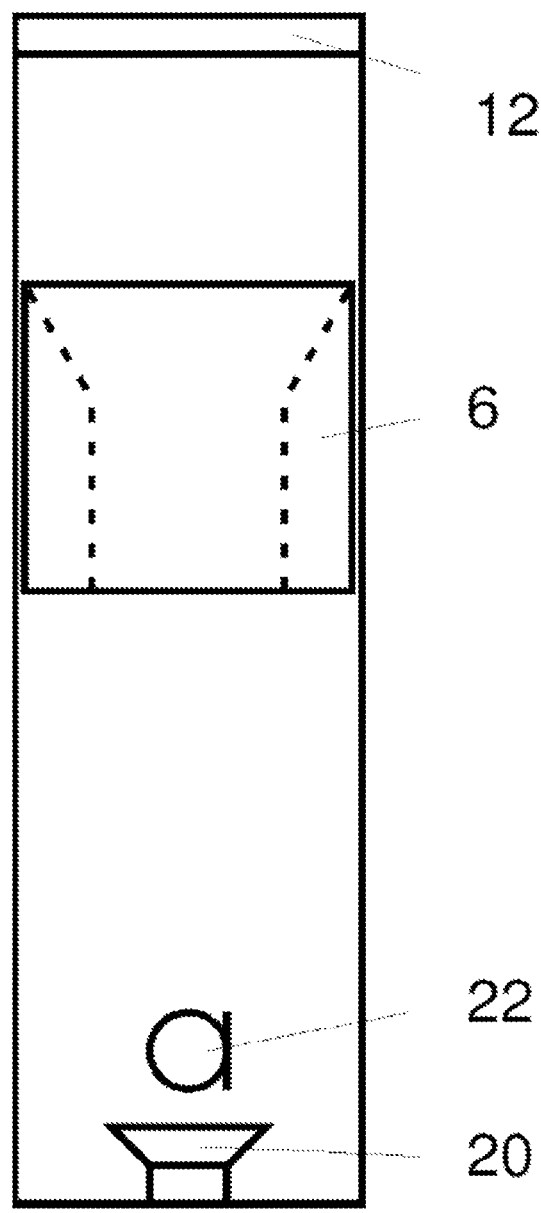
Figure 9:
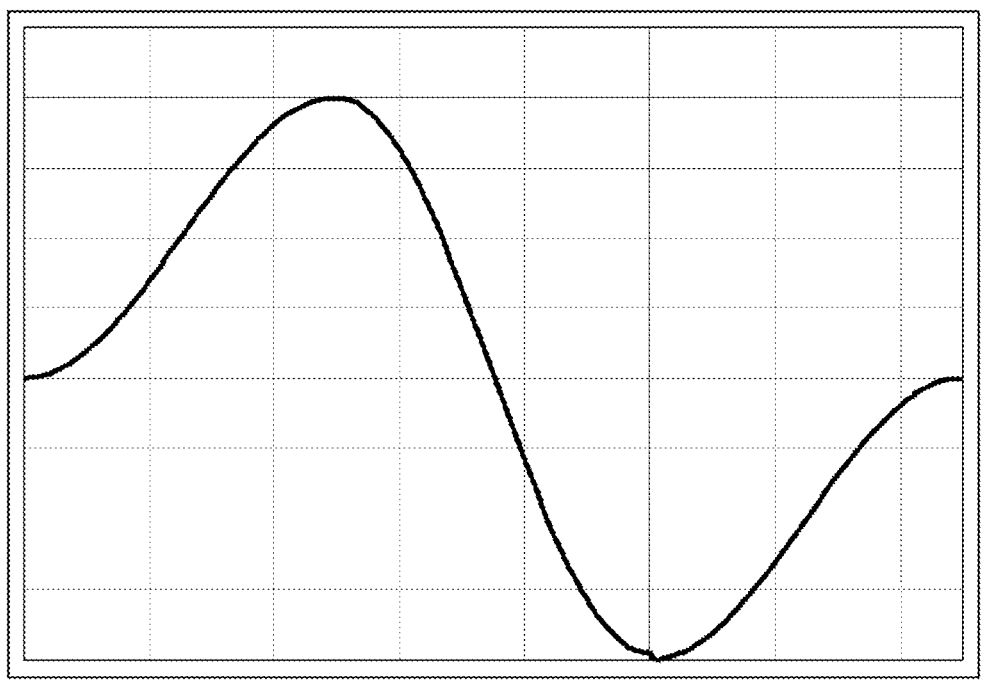
Figure 10:
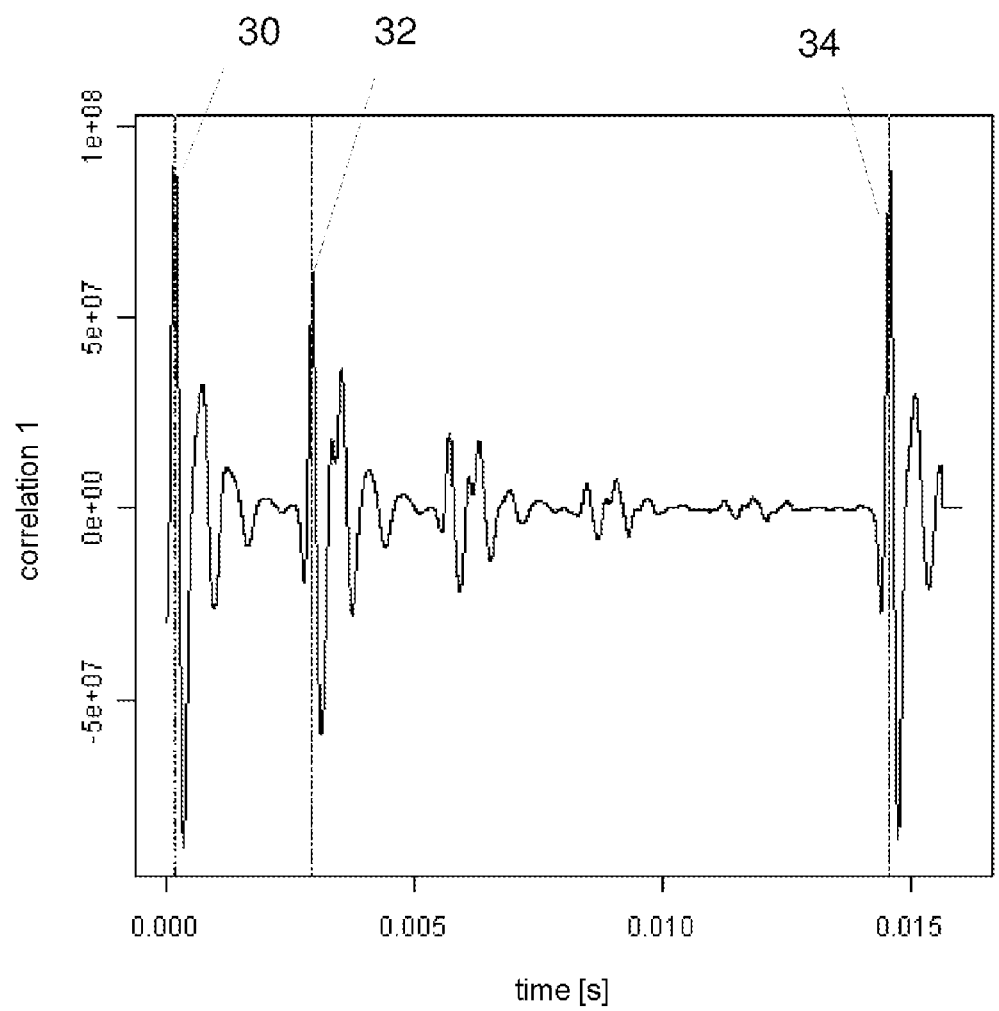
Figure 11:
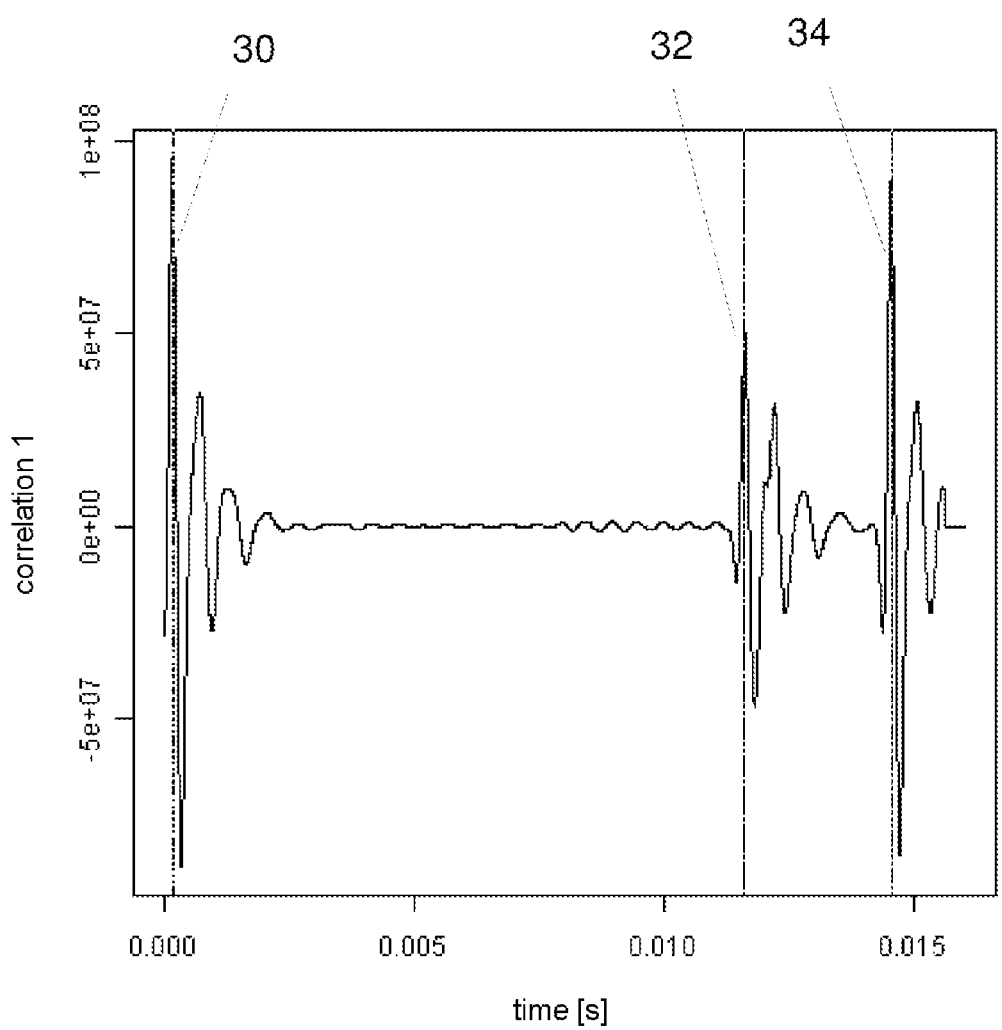

The invention will be described hereafter on the basis of an exemplary embodiment in conjunction with the drawings, in which:

FIG. 1 shows a schematic view of a length measuring device,

FIG. 2 shows an exploded view of parts of the length measuring device in the region of the measuring slide, FIG. 3 shows a cross-sectional view of the length measuring device in the region of inner slide and measuring slide, wherein the slide components themselves are not shown, but rather only the permanent magnets arranged therein, FIG. 4 shows a schematic view of the length measuring device in longitudinal section, FIG. 5 shows the excitation and the ringing of the ultrasonic transducer during emission of an ultrasound signal, FIG. 6 shows the digitized signals of the ultrasonic transducer in the course of its excitation to emit an ultrasound signal and the recording following thereto of a reflection signal as a function of time, FIG. 7 shows the cross-correlation of the excitation signal with the recorded reflected signal as a function of the time shift, FIG. 8 shows a schematic cross-sectional view of an alternative embodiment of a length measuring device, FIG. 9 shows an example of an exciting signal for a loudspeaker to generate an acoustic sound signal, FIG. 10 shows a cross-correlation of the emitted acoustic sound signal with the reflected sound signal recorded by the microphone at a first position of the inner slide, and FIG. 11 shows a cross-correlation of the emitted acoustic sound signal with the reflected sound signals recorded by the microphone at a second position of the inner slide.

DETAILED DESCRIPTION OF THE PREFERRED EMBODIMENTS

FIG. 1 shows a side view of a length measuring device, which can be fastened on a wall, for example. The length measuring device has a hollow profile 2 as a linear guide, on which a measuring slide 4, which carries a head plate 3, is mounted so it is externally displaceable. The measuring slide 4 is lowered until the head plate 3 rests from above on the head of the person to be measured.

An inner slide 6 is mounted so it is displaceable in the hollow profile 2, which is in the form of a circular ring in cross section in this exemplary embodiment. The inner slide 6 is also in the form of a circular ring in cross section, so that the inner slide 6 has a central passage opening 16. The external dimensions of the inner slide 6 are adapted to the internal dimensions of the hollow profile 2, so that the inner slide 6 is seated in the interior of the hollow profile 2 without play, but so it can slide. Correspondingly, the internal dimensions of the measuring slide 4 are adapted to the external dimensions of the hollow profile 2 so that the measuring slide 4 is mounted without play, but so it can slide, on the external circumference of the hollow profile 2.

FIG. 3 shows a cross section through the hollow profile 2 in the region of the measuring slide and the inner slide, wherein the measuring slide components and the inner slide components themselves are not shown, but rather only the magnet assembly made of multiple permanent magnets, which are introduced into the inner slide and the measuring slide. Four permanent magnets 7 are introduced into the inner slide 6 distributed around the circumference, which are distributed at an interval of 90° to one another around the circumference. Correspondingly, four permanent magnets 5 are also introduced into the measuring slide 4, which are arranged distributed in corresponding intervals of 90° around the external measuring slide. In this case, the arrangement of the permanent magnets is such that permanent magnets 5 and 7, which are opposite to one another, of the measuring slide 4 and the inner slide 6 are aligned having opposing poles toward one another. This is achieved in the illustrated exemplary embodiment in that the permanent magnets 7 of the inner slide are arranged oriented outward with one magnetic pole, in this example with the north pole, while the permanent magnets 5 are also arranged with this magnetic pole, the north pole here, oriented outward, so that in each case a pair of permanent magnets 5 and 7 oppose one another having opposing poles oriented toward one another. In this manner, the measuring slide 4 and the inner slide 6 are mechanically coupled to one another. The inner slide 6 thus follows every movement of the measuring slide 4 along the hollow profile 2. Only one of the permanent magnets 5 and 7 is shown in each case in FIG. 2.

Fundamentally, of course, more or fewer than four permanent magnets can also be provided per slide component, for example, only one permanent magnet in each case in the measuring slide 4 and the inner slide 6. It is even possible that only one magnet is provided overall in either the inner slide 6 or the measuring slide 4 and the other slide component contains ferromagnetic or paramagnetic material, without a separate magnet, so that magnetic attraction is caused between the inner slide 6 and the measuring slide 4. The magnet or magnets of the magnet assembly is/are preferably permanent magnets, however, electromagnets are fundamentally also usable.

FIG. 4 shows a schematic sectional view of the length measuring device to explain its mode of operation. An ultrasonic transducer 8 is arranged at one end of the hollow profile, in this example at the lower end, in the interior of the hollow profile 2. This transducer is connected to a control and analysis unit 10, which can advantageously also be arranged inside the hollow profile 2 or, as shown for reasons of simpler illustration ability, outside the hollow profile. The control and analysis unit 10 generates excitation signals for the ultrasonic transducer 8, which thereupon emits an ultrasound signal, which propagates upward in the hollow profile 2. The inner slide 6 has a lower wall region, which is formed by the lower end face of the slide in the form of a circular ring. A part of the emitted ultrasound signal is reflected on this lower wall region and runs back to the ultrasonic transducer 8. The distance between ultrasonic transducer 8 and the lower wall region of the inner slide 6 can be calculated by the measurement of the runtime from the emission of the ultrasonic signal from the ultrasonic transducer 8 until the capture of the signals reflected from the lower wall region of the inner slide 6, wherein the details of the calculation of the runtime will be discussed in greater detail hereafter.

A part of the ultrasound signal emitted from the ultrasonic transducer 8 passes through the inner slide 6, through its central passage opening 16, and propagates further in the hollow profile. In the illustrated exemplary embodiment, the hollow profile is closed on the opposite side by a wall 12. The part of the ultrasound signal passing the inner slide 6 is finally reflected on the wall 12 and passes through the passage opening 16 of the inner slide again back to the ultrasonic transducer 8. The runtime can also be determined for this part of the ultrasound signal. Since the absolute distance from the ultrasonic transducer 8 to the wall 12 of the hollow profile is known, a calibration of the distance determination can thus be carried out from the runtime measurement.

Fundamentally, another reflected signal can also be used for such a calibration; for example, a part of the ultrasound signal is also reflected at the upper end of the passage opening 16. With known axial length of the inner slide 6 in the longitudinal direction of the hollow profile, a calibration of the distance determination from the runtime can be carried out from the runtime difference between the ultrasound signal reflected on the lower wall region of the inner slide 6 and that reflected on the upper end of the passage opening 16 of the inner slide. To amplify the reflection at the upper edge of the passage opening 16, an inwardly protruding wall region can also be provided on this upper edge, so that an inwardly oriented shoulder is implemented at the upper end of the passage opening 16. Generally, other discontinuities can also be provided in the interior of the hollow profile, which generate reflections of an ultrasound signal emitted from the ultrasonic transducer 8 and, with known positions along the hollow profile, a calibration of the distance determination from the runtime measurement can again be performed from the runtimes thereof.

FIG. 5 shows the amplitude of the excitation of the ultrasonic transducer 8 and the subsequent ringing (post-pulse oscillation) of the ultrasonic transducer as a function of time. The control and analysis unit 10 excites the ultrasonic transducer 8 using five pulses having a period duration of 25 µs (1/40 kHz), after which a phase jump by 180° and then five further pulses of equal pulse length follow. The phase jump of 180° is shown in the increased interval between the fifth and sixth pulses of the pulse sequence. The ultrasonic transducer than continues to ring for a certain time as shown.

A characteristic point of the emitted ultrasound signal, which also has to be displayed in the reflected signal, is used to calculate the distance. Such a characteristic point can be, for example, a phase jump, an amplitude jump, or a frequency jump. The signal recorded after emitting the ultrasound signal from the ultrasonic transducer is sampled and digitized at a high sampling rate in comparison to the ultrasound frequency of, for example, $f_S$=500 kHz. If the sampling point of the recorded reflection signal at which the characteristic point of the emitted signal is recovered, the runtime can be calculated therefrom. If the number of the sampling point, at which the characteristic point is recovered in the reflection signal, from the sampling point at which the characteristic point occurs in the emitted signal is identified with $N_S$, the following equation thus results therefrom for the distance L of the reflection point:

$$L = \frac{N_S c_l}{2 f_s}$$

In this case, $N_S$ is the number of the sampling point at which the characteristic point occurred in the reflected signal, counted from the sampling point of the characteristic point of the emitted signal, $c_l$ is the speed of sound, and $f_S$ is the sampling frequency, for example, $f_S$=500 kHz.

In the case of such a measurement, the theoretical resolution is determined by the sampling frequency and the following results for $f_S$=500 kHz:

$$\Delta L = \frac{c_l}{2 f_s} \approx 0.343 \text{ mm}$$

Such a precision is acceptable for the length measurement to determine the physical height of persons.

To find the characteristic point of the emitted signal in the reflected signal, for example, a cross-correlation can be calculated. In the case of sampled digitized signals, the cross-correlation for discrete systems can be described as follows:

$$F(n) = \sum_{l=1}^{M} S(l+n) \cdot W(l)$$

S is the digitized signal received by the ultrasonic transducer and W is a digitized function corresponding to the emitted signal, M is a predetermined number of sampling points, which corresponds to a window length. The cross-correlation F is greatest when the shift of the function characterizing the emitted signal just results precisely in the reflected signal, so that the characteristic point of the emitted signal is coincident with the characteristic point of the reflected signal.

FIG. 6 shows the output of the ultrasonic transducer as a function of time after an excitation as illustrated in FIG. 5. After the excitation and the ringing of the ultrasonic transducer, no reflections are initially recorded for a time up to approximately 6 ms. In the period of time from approximately 6 ms to 10 ms, the output amplitude of the ultrasonic transducer is increased by the first reflection. FIG. 7 shows the cross-correlation as a function of the time shift between emitted signal and reflected signal. The cross-correlation reaches its maximum at approximately 6.2 ms. This maximum of the cross-correlation is used to determine the runtime of the reflection.

In this case, this reflection occurs on the lower wall region of the inner slide. In the same manner, a further reflection, for example, from the upper end of the hollow profile, can be recorded and the runtime for this further reflection can again be determined by forming the cross-correlation. Since the distance of the ultrasonic transducer to the point of the further reflection or the distance to the first reflection is known, the distance measurement as a function of the runtime can be absolutely calibrated by such a reference measurement.

FIG. 8 shows a schematic cross-sectional illustration of an alternative embodiment of a length measuring device, wherein the measuring slide is not shown externally on the hollow profile here for simplification. In the interior of the hollow profile, a loudspeaker 20, which is capable of generating an acoustic sound signal, is located at its lower end. An acoustic sound signal is understood in the present application as a signal having sound wavelengths in the audible range.

The acoustic sound signal, to which the loudspeaker 20 is excited by the control and analysis unit, represents a short sound pulse, which sounds practically like a short "crackle". The runtimes of the sound waves up to the lower end of the measuring slide and the runtime from the loudspeaker to the end wall and back to the microphone may be ascertained by way of the echoes, which are generated by reflections on the lower end region of the inner slide and, for example, on the end wall of the hollow profile, whereby the position of the inner slide along the longitudinal axis of the hollow profile may be derived together with a reference measurement for calibration.

The control and analysis unit, which is not shown in FIG. 8 for simplification, is configured to activate the loudspeaker 20 so that it emits a short pulse of an acoustic sound signal. This pulse propagates in the interior of the hollow profile and is captured by a microphone 22. The pulse propagates further and is incident on the lower edge of the inner slide 6, which reflects a part of the acoustic sound signal. The reflected component of the pulse then runs back again and is incident on the microphone 22. The inner slide 6 again has a passage 16, which enables a part of the pulse of the acoustic sound signal to pass the inner slide 6. This component then propagates further in the hollow profile 2, until it is incident on the end wall 12 and is reflected thereon, upon which a part again passes the passage 16 of the inner slide 6 and finally reaches the microphone 22 again. The distance between the microphone 22 and the end wall 12 is constant and known, so that an absolute calibration of the distance measurement is possible by way of the measurement of the runtime of the signal reflected on the end wall 12.

The passage 16 through the inner slide 6 is designed in this exemplary embodiment so that as little sound as possible is reflected on the end of the passage 16 facing away from the loudspeaker 20, to prevent losses and to obtain a maximum reflection on the end wall 12. In an alternative embodiment, however, the passage 16 can also be designed as in the first exemplary embodiment, so that a second reflection takes place on the end of the passage 16 facing away from the loudspeaker 20, so that in each case a double signal of sound waves reflected on the inner slide 6 is captured, wherein the spacing of the signals in this double signal can be related to the known axial length of the inner slide 6, to obtain an absolute calibration of the distance determination.

FIG. 9 shows an example of an exciting signal for the loudspeaker as a function of time. The signal is selected so that the loudspeaker is continuously started and shut down again; i.e., the illustrated positive and negative half wave is not sinusoidal, but rather is modified so that the slope is zero at the beginning of the positive half wave and at the end of the negative half wave. If the loudspeaker were abruptly started at the beginning or abruptly stopped at the end, harmonics would be excited, which are not desired. The pulse duration of the signal in FIG. 9 is 0.375 ms.

In this example, a cross-correlation is formed between the exciting signal and the signal recorded using the microphone. This provides a cross-correlation as shown in FIGS. 10 and 11. In FIG. 10, the inner slide is located relatively close to the microphone in this case. In this situation, a first maximum 30 of the cross-correlation occurs, which reflects the distance between loudspeaker 20 and microphone 22. The second maximum 32 of the cross-correlation corresponds to the first sound signal reflected on the lower wall region of the inner slide. In the illustrated example, the slide is located relatively close to the microphone, so that the first sound signal reflected on the inner slide 6 is incident again on the microphone after a relatively short delay time. The third maximum 34 of the cross-correlation corresponds to the acoustic sound signal reflected on the end wall 12 of the hollow profile, which thus results in the runtime between loudspeaker 20 and the end wall 12 and back to the microphone 22.

FIG. 11 shows a cross-correlation corresponding to FIG. 10, wherein in this case the inner slide is located at a greater distance to the microphone 22, so that the time delay up to the second maximum 32 of the cross-correlation is accordingly greater.

The runtime $T_{meas}$ between the direct signal at the first maximum 30 of the cross-correlation and the first echo corresponding to the second maximum 32 is ascertained from the cross-correlations, which originates from the reflection of the acoustic sound signal on the lower end wall region of the inner slide 6. In addition, the runtime $T_{ref}$ between the direct signal at the first maximum 30 of the cross-correlation and the echo of the end wall 12 is ascertained, which corresponds to the third maximum 34 of the cross-correlation. For the distances, the following equations then apply $$D_{meas} = \frac{T_{meas}}{2} \cdot C$$

$$D_{ref} = \frac{T_{ref}}{2} \cdot C$$

wherein C is the speed of sound, $D_{meas}$ is the distance between microphone and inner slide, and $D_{ref}$ is the distance between microphone and end wall 12.

Therefore, the following equation results for the distance sought:

$$D_{meas} = \frac{T_{meas}}{T_{ref}} \cdot D_{ref}$$

LIST OF REFERENCE NUMERALS

2 hollow profile
3 head plate
4 measuring slide
5 permanent magnet in the measuring slide
6 inner slide
7 permanent magnet in the inner slide
8 ultrasonic transducer
10 control and analysis unit
12 end wall
20 loudspeaker
22 microphone
30 acoustic sound signal
32 reflected signal of the inner slide
34 reflected signal of the end wall

The invention claimed is:

1. A length measuring device comprising:
a measuring slide,
a linear guide comprising a hollow profile, on which the measuring slide is mounted so as to be externally displaceable, to be able to bring the measuring slide into contact with an object to be measured with respect to an object length,
an inner slide, which is mounted so as to be displaceable in an interior of the hollow profile,
a magnet assembly, which magnetically couples the measuring slide and the inner slide, so that the inner slide follows every movement of the measuring slide along the hollow profile,
a measuring unit for measuring a position of the inner slide along the hollow profile, and
a display, which is visible in an exterior of the hollow profile, of a measured object length ascertained by the measuring unit in accordance with the measured position of the inner slide,
wherein the measuring unit includes a sound source, a sound receiver, and a control and analysis unit connected to the sound source and the sound receiver,
wherein the control and analysis unit is configured to excite the sound source to emit a sound signal and to analyze representative output signals of the sound receiver, to determine a runtime of a first reflected sound signal reflected on the inner slide at a reflection location and to calculate the position of the inner slide along the hollow profile,
wherein the control and analysis unit is furthermore configured to capture a further reflected sound signal represented in the output signals of the sound receiver, wherein the further reflected signal has been reflected at a known point along the hollow profile or at a known distance from the reflection location of the first reflected sound signal, and to cause a runtime of the further reflected sound signal to be incorporated as a reference measurement in the calculation of the position of the inner slide.

2. The length measuring device as claimed in claim 1,
wherein the sound source and sound receiver are arranged in an end region of the hollow profile, and
wherein the control and analysis unit is configured to determine the runtime of the first reflected sound signal, which was reflected from a lower wall region of the inner slide facing toward the sound source,
wherein the inner slide comprises a ring-shaped structure including a passage opening extending in an axial direction,
wherein the control and analysis unit is configured to register the further reflected sound signal, which is reflected on an end of the ring-shaped structure facing away from the sound source and returns to the sound receiver.

3. The length measuring device as claimed in claim 2,
wherein discontinuities are arranged in the hollow profile at predetermined positions, said discontinuities generating reflections of sound signals, and
wherein the control and analysis unit is configured to capture the reflections of sound signals, represented as further reflected signals in the output signals of the sound receiver, and to have runtimes of the reflections of sound signals incorporated as further reference measurements in the calculation of the position of the inner slide.

4. The length measuring device as claimed in claim 1,
wherein the sound source is arranged in an end region of the hollow profile,
wherein the control and analysis unit is configured to determine the runtime of the first reflected sound signal, which was reflected from a lower wall region of the inner slide facing toward the sound source,
wherein the inner slide comprises a ring-shaped structure including a passage opening extending in an axial direction, and
wherein the hollow profile is closed on an end opposite the sound source by an end wall, wherein the control and analysis unit is configured to register the further reflected sound signal, after it has passed the passage opening of the inner slide and has been reflected on the end wall on the opposing closed end of the hollow profile and has returned to the sound receiver.

5. The length measuring device as claimed in claim 4,
wherein discontinuities are arranged in the hollow profile at predetermined positions, said discontinuities generating reflections of sound signals, and
wherein the control and analysis unit is configured to capture the reflections of sound signals, represented as further reflected signals in the output signals of the sound receiver, and to have runtimes of the reflections of sound signals incorporated as further reference measurements in the calculation of the position of the inner slide.

6. The length measuring device as claimed in claim 1,
wherein discontinuities are arranged in the hollow profile at predetermined positions, said discontinuities generating reflections of sound signals, and
wherein the control and analysis unit is configured to capture the reflections of sound signals, represented as further reflected signals in the output signals of the sound receiver, and to have runtimes of the reflections of sound signals incorporated as further reference measurements in the calculation of the position of the inner slide.

7. The length measuring device as claimed in claim 1,
wherein the hollow profile is completely closed, so that the interior of the hollow profile is configured to be closed off in relation to an environment.

8. The length measuring device as claimed in claim 1,
wherein the control and analysis unit is configured to carry out a distance determination from at least one of said runtime measurements via a time of flight (TOF) method.

9. The length measuring device as claimed in claim 1,
wherein the control and analysis unit is configured to excite the sound source using a periodic excitation signal, to which a characteristic signal property is superimposed, and to calculate the runtime by forming a correlation of the reflected signals recorded by the sound receiver with the excitation signal, in particular to calculate a cross-correlation and to determine the runtime at the maximum of the cross-correlation.

10. The length measuring device as claimed in claim 9, said characteristic signal property comprising a phase jump, an amplitude jump, or a frequency jump.

11. The length measuring device as claimed in claim 1,
wherein the magnet assembly includes at least one permanent magnet on the measuring slide and a permanent magnet on the inner slide, which are arranged so that opposing poles of the two permanent magnets are aligned in relation to one another facing toward one another.

12. The length measuring device as claimed in claim 11,
wherein four of said permanent magnets on the inner slide and four of said permanent magnets on the measuring slide are arranged in relation to one another such that pairs of permanent magnets on the measuring slide and on the inner slide are aligned in relation to one another having opposing poles facing toward one another.

13. The length measuring device as claimed in claim 1,
wherein the magnet assembly includes one permanent magnet on one of the measuring slide and the inner slide, and the other of the measuring slide and the inner slide contains ferromagnetic material or paramagnetic material.

14. The length measuring device as claimed in claim 1,
wherein an internal diameter of the hollow profile is selected and the sound source and the control and analysis unit are configured such that the internal diameter of the hollow profile is less than half of the wavelength of the sound signal.

15. The length measuring device as claimed in claim 1,
wherein the sound source is an ultrasound source and the sound receiver is an ultrasound receiver.

16. The length measuring device as claimed in claim 15,
wherein the ultrasound source and the ultrasound receiver are formed by a unified ultrasonic transducer comprising a transceiver.

17. The length measuring device as claimed in claim 1,
wherein the sound source comprises a loudspeaker for generating the sound signal acoustically and the sound receiver comprises a microphone for acoustically recording acoustic the reflected sound signals.

* * * * *